(12) United States Patent
Augustine et al.

(10) Patent No.: US 8,283,602 B2
(45) Date of Patent: Oct. 9, 2012

(54) HEATING BLANKET

(75) Inventors: Scott D. Augustine, Bloomington, MN (US); Randall C. Arnold, Minnetonka, MN (US); Ryan S. Augustine, Minneapolis, MN (US); Rudolf A. Deibel, Eden Prairie, MN (US); Scott A. Entenman, St. Paul, MN (US); Gordon D. Lawrence, Minneapolis, MN (US); Keith J. Leland, Medina, MN (US); Thomas F. Neils, Minneapolis, MN (US)

(73) Assignee: Augustine Temperature Management LLC, Eden Prairie, MN (US)

( * ) Notice: Subject to any disclaimer, the term of this patent is extended or adjusted under 35 U.S.C. 154(b) by 878 days.

(21) Appl. No.: 12/050,806

(22) Filed: Mar. 18, 2008

(65) Prior Publication Data

US 2008/0230530 A1    Sep. 25, 2008

Related U.S. Application Data

(60) Provisional application No. 60/895,736, filed on Mar. 19, 2007.

(51) Int. Cl.
*H05B 3/00* (2006.01)
*H05B 3/34* (2006.01)

(52) U.S. Cl. ........ 219/212; 219/211; 219/217; 219/505; 219/528; 219/529; 219/544; 219/545; 219/548; 219/549; 219/552; 219/553

(58) Field of Classification Search ............. 219/211–2, 219/528–529, 544–5, 548–9, 552–3, 505, 219/217
See application file for complete search history.

(56) References Cited

U.S. PATENT DOCUMENTS

| 3,808,403 | A | | 4/1974 | Kanaya et al. |
| 3,900,654 | A | | 8/1975 | Stinger |
| 3,936,661 | A | | 2/1976 | Furuishi et al. |
| 4,061,898 | A | | 12/1977 | Murray et al. |
| 4,149,066 | A | | 4/1979 | Niibe |
| 4,479,795 | A | | 10/1984 | Mustacich et al. |
| 4,534,886 | A | * | 8/1985 | Kraus et al. ............ 252/502 |
| 4,626,664 | A | | 12/1986 | Grise |
| 4,719,335 | A | | 1/1988 | Batliwalla et al. |
| 4,764,665 | A | | 8/1988 | Orban et al. |
| 4,798,936 | A | | 1/1989 | Johnson, Sr. |
| 4,912,306 | A | | 3/1990 | Grise et al. |
| 5,008,515 | A | | 4/1991 | McCormack |
| 5,010,233 | A | | 4/1991 | Henschen et al. |
| 5,023,433 | A | | 6/1991 | Gordon |
| 5,380,580 | A | | 1/1995 | Rogers et al. |

(Continued)

FOREIGN PATENT DOCUMENTS

GB        586745        3/1947

OTHER PUBLICATIONS

EeonTex™ Conductive Testiles, Product Details, www.eeonyx.com/prodte.html, Sep. 19, 2006, pp. 1-5.

(Continued)

*Primary Examiner* — Shawntina Fuqua
(74) *Attorney, Agent, or Firm* — Fredrikson & Byron, P.A.

(57) ABSTRACT

An electric heating blanket including a flexible sheet-like heating element and a shell. The shell covers the heating blanket an includes two sheets of flexible material welded together.

40 Claims, 15 Drawing Sheets

U.S. PATENT DOCUMENTS

| | | | |
|---|---|---|---|
| 5,422,462 A | 6/1995 | Kishimoto | |
| 5,443,056 A | 8/1995 | Smith et al. | |
| 5,773,275 A | 6/1998 | Anderson et al. | |
| 5,817,145 A | 10/1998 | Augustine et al. | |
| 5,824,996 A | 10/1998 | Kochman et al. | |
| 5,928,274 A | 7/1999 | Augustine | |
| 5,964,792 A | 10/1999 | Augustine | |
| 5,974,605 A | 11/1999 | Dickerhoff et al. | |
| 5,986,243 A | 11/1999 | Campf | |
| 6,078,026 A | 6/2000 | West | |
| 6,093,910 A | 7/2000 | McClintock et al. | |
| 6,172,344 B1 | 1/2001 | Gordon et al. | |
| 6,184,496 B1 | 2/2001 | Pearce | |
| 6,235,049 B1 | 5/2001 | Nazerian | |
| 6,373,034 B1 | 4/2002 | Rock et al. | |
| 6,403,935 B2 | 6/2002 | Kochman et al. | |
| 6,483,087 B2 | 11/2002 | Gardner et al. | |
| 6,582,456 B1 | 6/2003 | Hand et al. | |
| 6,770,848 B2 | 8/2004 | Haas et al. | |
| 6,770,854 B1 | 8/2004 | Keane | |
| 6,839,922 B1 * | 1/2005 | Foggett et al. | 5/421 |
| 6,974,935 B2 | 12/2005 | O'Grady | |
| 7,022,950 B2 | 4/2006 | Haas et al. | |
| 7,053,344 B1 | 5/2006 | Surjan et al. | |
| 2002/0005398 A1 | 1/2002 | Gillner et al. | |
| 2002/0117495 A1 | 8/2002 | Kochman et al. | |
| 2005/0016982 A1 | 1/2005 | Campf et al. | |

OTHER PUBLICATIONS

Stoll & Greene, "Relationship Between Pain and Tissue Damage Due to Thermal Radiation", J. Applied Physiology 14 (3):373-382, 1959.

Moritz and Henriques, "Studies of Thermal Injury: The Relative Importance of Time and Surface Temperature in the Causation of Cutaneous Burns", Am. J. Pathology 23:695-720, 1947.

* cited by examiner

HEATING BLANKET

CROSS-REFERENCE TO RELATED APPLICATION

This application claims priority under 35 U.S.C. §119(e) to co-pending U.S. provisional application 60/895,736, filed Mar. 19, 2007, which is hereby incorporated by reference in its entirety.

TECHNICAL FIELD

The present invention is related to heating or warming blankets or pads and more particularly to those including electrical heating elements.

BACKGROUND

It is well established that surgical patients under anesthesia become poikilothermic. This means that the patients lose their ability to control their body temperature and will take on or lose heat depending on the temperature of the environment. Since modern operating rooms are all air conditioned to a relatively low temperature for surgeon comfort, the majority of patients undergoing general anesthesia will lose heat and become clinically hypothermic if not warmed.

Over the past 15 years, forced-air warming (FAW) has become the "standard of care" for preventing and treating the hypothermia caused by anesthesia and surgery. FAW consists of a large heater/blower attached by a hose to an inflatable air blanket. The warm air is distributed over the patient within the chambers of the blanket and then is exhausted onto the patient through holes in the bottom surface of the blanket.

Although FAW is clinically effective, it suffers from several problems including: a relatively high price; air blowing in the operating room, which can be noisy and can potentially contaminate the surgical field; and bulkiness, which, at times, may obscure the view of the surgeon. Moreover, the low specific heat of air and the rapid loss of heat from air require that the temperature of the air, as it leaves the hose, be dangerously high—in some products as high as 45° C. This poses significant dangers for the patient. Second and third degree burns have occurred both because of contact between the hose and the patient's skin, and by blowing hot air directly from the hose onto the skin without connecting a blanket to the hose. This condition is common enough to have its own name—"hosing." The manufacturers of forced air warming equipment actively warn their users against hosing and the risks it poses to the patient.

To overcome the aforementioned problems with FAW, several companies have developed electric warming blankets. Some of these warming blankets employ flexible heaters, the flexibility of which is desirable to maintain when employing the blankets. In many cases, an electric warming blanket employs a shell for holding the heater and for serving other purposes. For example, in some cases the shell includes layers formed of a substantially water impermeable material to help prevent fluid damage to the heater. Also, when these heaters are used for patient or other care, especially in the operating room, the shell can protect the patient and others in the vicinity from electric shock hazards. In addition to often providing a seal around the heater, the shell often contains a fastening mechanism that must reliably attach the heater to the shell to prevent electrical shorting across the heater during folding of the electric warming blanket.

Because the seals of the shell must be very reliable, the seals have traditionally been adhesive seals that are reinforced with combinations of sewing, rivets, and grommets. Sewing stitches, rivets, and grommets all share one characteristic—they all perforate the material layers to create a mechanical linkage between the layers.

While such a reinforced bond may be desirable for strength, it can create additional problems when used during surgery or medical procedures. For example, heated blankets placed over a patient during a surgery or medical procedure are frequently soiled with waste blood or other body fluids. The fluid waste can saturate the stitching and then dry and accumulate in the thread or the stitch holes. If rivets or grommets are used for reinforcement, additional crevasses are introduced that can trap waste fluids. When the outer shell of the blanket is cleaned by hospital personnel, it is nearly impossible to clean the residual contaminating materials out of the holes, crevasses, and/or stitches. Therefore, the stitching holes and thread, the grommets, rivets and snaps can all become sources of microbial contamination because they can not be thoroughly cleaned and disinfected.

Accordingly, there remains a need for heated blankets and shells for flexible heaters that is readily and thoroughly cleanable. Various embodiments of the invention described herein solve one or more of the problems discussed above in addition to other problems that will become apparent.

SUMMARY

Certain embodiments of the invention include an electric heating blanket including a flexible sheet-like heating element and a shell. The shell covers the heating blanket an includes two sheets of flexible material welded together. In some embodiments the weld couples the sheets together about the edges of the heating element. In some embodiments, the weld couples the sheets about the edges of the sheets.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized. The term 'blanket', used to describe embodiments of the present invention, may be considered to encompass heating blankets and pads.

Figure 1:
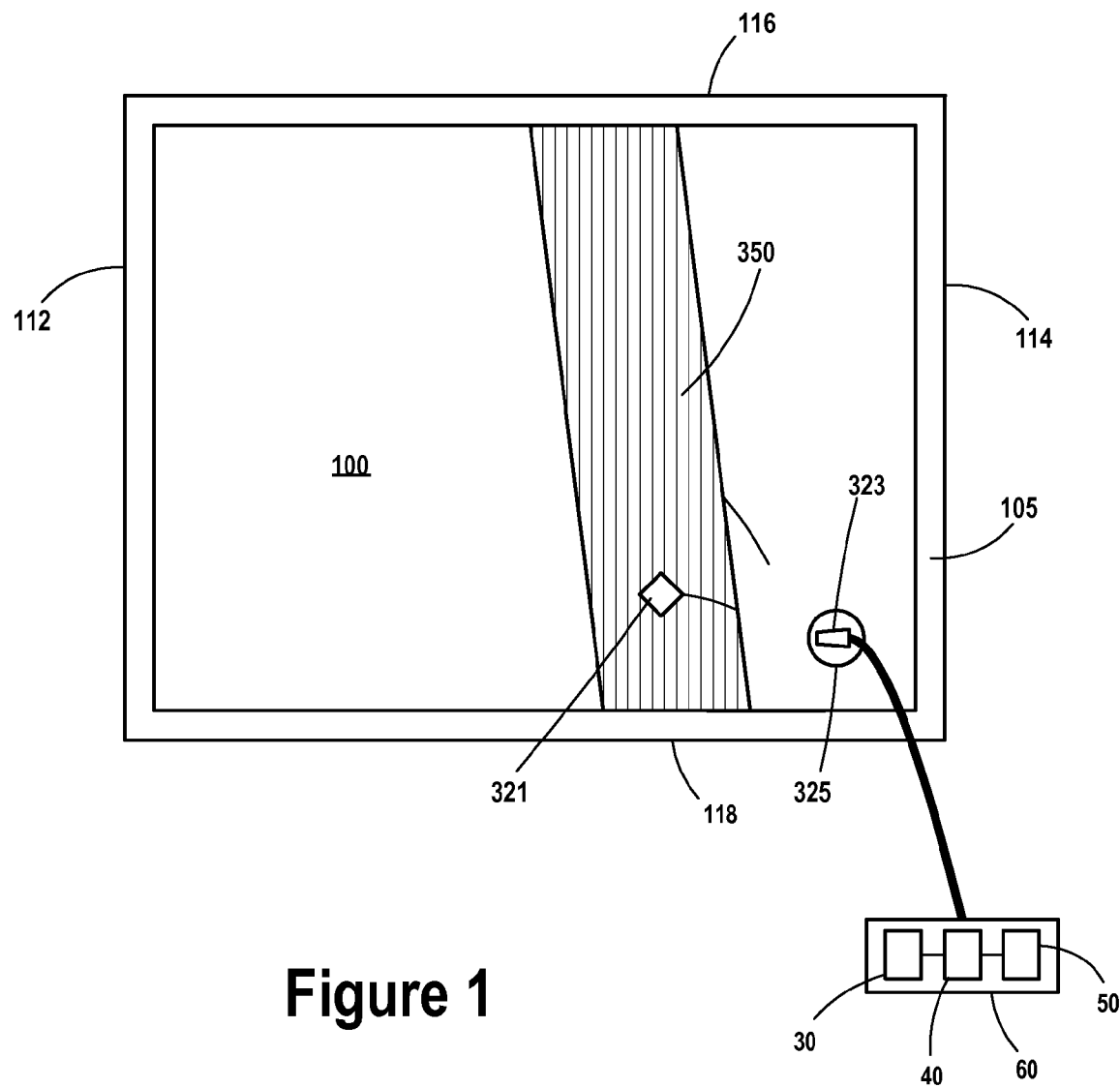
FIG. 1 is a top plan view of a heating blanket, according to some embodiments of the present invention.

FIG. 1 shows a heating blanket 100 according to some embodiments of the present invention. As shown, the heating blanket 100 is generally rectangular. Embodiments of the present invention can be used in connection with a wide variety of heating blankets. For example, in some cases, the heating blanket can be a blanket sized and shaped for the upper body or upper body limb (e.g., a wrap-around blanket), or a blanket sized and shaped for the lower body or lower body limb. In some cases the heating blanket can be used in conjunction with a disposable cover.

The heating blanket 100 of FIG. 1 includes a shell 105 that can be durable and waterproof. As shown, a portion of the shell 105 is cut away, revealing a heating element assembly 350. The heating element assembly 350 is generally covered by the shell and can extend within the shell 105 between edge 112 and edge 114 and between edge 116 and edge 118. An electrical connector housing 325 and a corresponding connector plug 323 can be coupled to the shell 105, thereby enabling access to a temperature sensor assembly such as those discussed below.

The shell 105 can protect and isolate the heating element assembly 350 from an external environment of heating blanket 100. The shell 105 can include a water-resistant material layer that can form a substantially hermetic seal around the heating element assembly 350. The shell 105 can provide further protection to a patient disposed beneath heating blanket 100 against electrical shock hazards. According to preferred embodiments of the present invention, shell 105 is waterproof to prevent fluids (e.g., bodily fluids, IV fluids, cleaning fluids, etc.) from contacting the heating element assembly 350. In some preferred embodiments, shell 105 may further include an anti-microbial element (e.g., a SILVERion™ antimicrobial fabric available from Domestic Fabrics Corporation or Ultra-Fresh™ from Thomson Research Associates).

According to an illustrative embodiment of the present invention, shell 105 comprises a nylon fabric having an overlay of polyurethane coating to provide waterproofing. The coating can be on at least an inner surface of each of the two sheets, further facilitating a heat seal between the two sheets, according to preferred embodiments. In other embodiments, the shell 105 comprises polyvinyl chloride (PVC) to facilitate an RF weld to bond the sheets. It should be noted that, according to some embodiments of the present invention, a covering for heating element assemblies may be removable and, thus, include a reversible closure facilitating removal of a heating element assembly 350 therefrom and insertion of the same or another heating element assembly 350 therein. In some embodiments, shell 105 comprises a PVC film of sufficient thickness to provide the necessary strength. In some such embodiments, the edge seals can be softer.

In some embodiments, one or more layers may be positioned between the heating element assembly 350 and the shell 105. For example, in some embodiments, a layer of thermally insulating material (e.g., polymeric foam or high-loft fibrous non-woven material) can be included in one or more locations. In some instances, a layer of thermally insulating material can be positioned to protect a portion of the patient from the heating element assembly 350 in the event that part of the shell 105 is inadvertently placed under that portion of the patient. In such instances, a layer of thermal insulating material can be positioned between the heating element assembly 350 and the patient-contacting surface of the shell 105. In this way, in the event that part of the shell 105 is inadvertently placed under that portion of the patient, that portion of the patient can contact an insulated portion of the shell 105 rather than a non-insulated portion of the shell 105.

In some instances a layer of thermally insulating material can be positioned to make sure that a maximal amount of heat being generated by the heating element assembly 350 is transferred to the patient. In such instances, a layer of thermally insulating material can help insulate the heating element assembly 350 from the environment and provide a more uniform temperature distribution. The layer of thermally insulating material can be positioned between the heating element assembly 350 and the surface of the shell 105 that does not contact the patient. In this way, a maximal amount of heat being generated by the heating element assembly 350 can be transferred to the patient and not to the surrounding environment.

In some instances a layer of thermally insulating material can be positioned to prevent caregivers from experiencing unwanted contact with activated heating blankets. Other layers (e.g., an electrically insulating layer similar to those discussed elsewhere herein) can be positioned between the heating element assembly 350 and the shell 105.

Figure 2A:
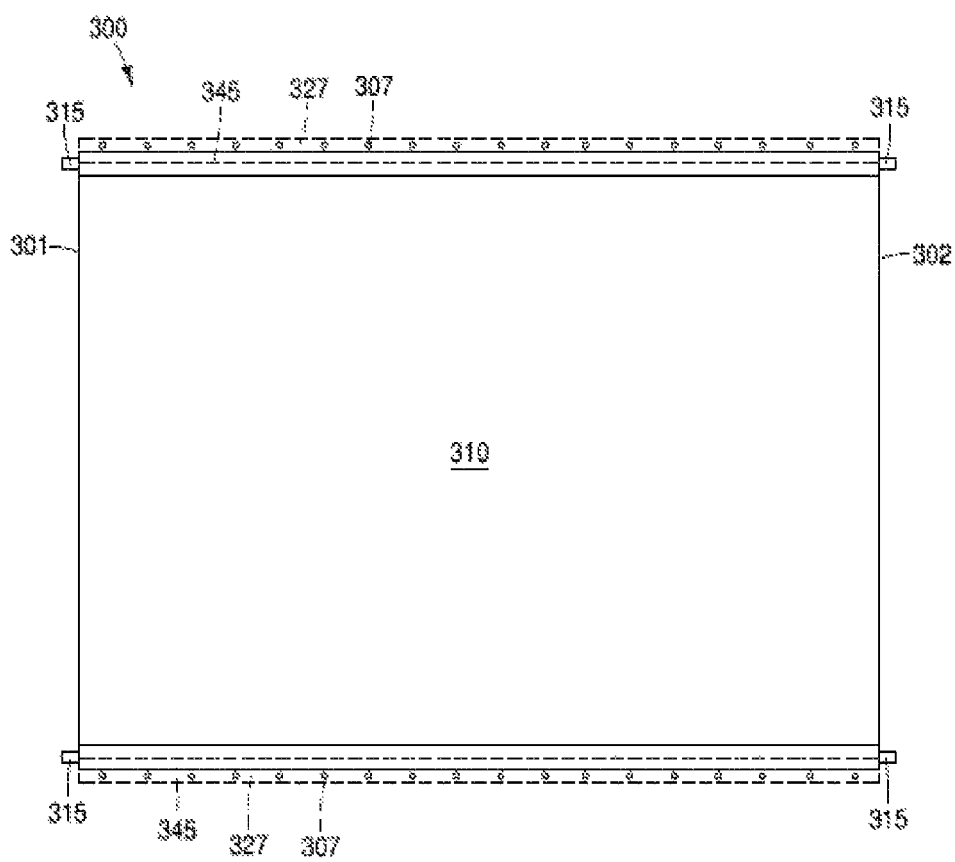
FIG. 2A is a plan view of a flexible heating blanket subassembly for a heating blanket, according to some embodiments of the present invention.
Figure 2B:
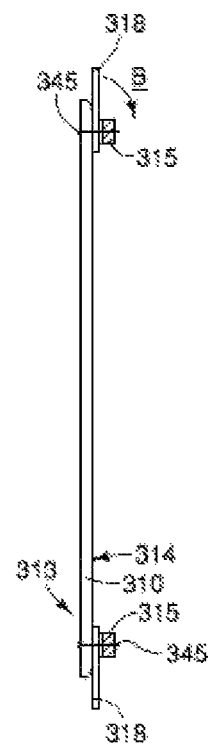
FIG. 2B is an end view of some embodiments of the subassembly shown in FIG. 2A.

FIGS. 2A-2B show an illustrative heating blanket subassembly 300 that can be incorporated into heating element assemblies (e.g., heating element assembly 350 of FIG. 1) in some embodiments of the present invention. Referring again to FIGS. 2A-2B, in many embodiments, the heating blanket subassembly 300 is flexible. The heating blanket subassembly 300 can include a flexible sheet-like heating element 310, or heater, which can include a first side edge 301 and a second side edge 302. According to preferred embodiments of the present invention, heating element 310 comprises a conductive fabric or a fabric incorporating closely spaced conductive elements such that heating element 310 has a substantially uniform watt density output, preferably less than approximately 0.5 watts/sq. inch, and more preferably between approximately 0.2 and approximately 0.4 watts/sq. inch, across a surface area, of one or both sides 313, 314 (FIG. 2B).

Some examples of conductive fabrics which may be employed by embodiments of the present invention include, without limitation, carbon fiber fabrics, fabrics made from carbonized fibers, conductive films, or woven or non-woven non-conductive fabric or film substrates coated with a conductive material, for example, polypyrrole, carbonized ink, or metalized ink. In many embodiments, the conductive fabric is a polymeric fabric coated with a conductive polymeric material such as polypyrrole. In addition, the flexible heating element 310 may be made from a matrix of electrically resistant wire or metal traces attached to a fibrous or film material layer.

FIG. 2A further illustrates subassembly 300 including two bus bars 315 coupled to heating element 310 for powering heating element 310. Each bar 315 is shown extending between first and second side edges 301, 302. With reference to FIG. 2B, according to some embodiments, bus bars 315 are coupled to heating element 310 by a stitched coupling 345 (e.g., formed with conductive thread such as silver-coated polyester or nylon thread (Marktek Inc., Chesterfield, Mo.)).

As shown, insulation is provided between the bus bars 315 and the heating element 310. FIG. 2B illustrates subassembly 300 wherein insulating members 318 (e.g., fiberglass material strips having an optional PTFE coating and a thickness of approximately 0.003 inch) extend between bus bars 315 and heating element 310 at each stitched coupling 345, so that electrical contact points between bars 315 and heating element 310 are solely defined by the conductive thread of stitched couplings 345. Alternatively, the electrical insulation material layer could be made of polymeric film, a polymeric film reinforced with a fibrous material, a cellulose material, a glass fibrous material, rubber sheeting, polymeric or rubber coated fabric or woven materials or any other suitable electrically insulating material.

Each of the conductive thread stitches of coupling 345 can maintain a stable and constant contact with bus bar 315 on one side and heating element 310 on the other side of insulating member 318. The stitches produce a stable contact in the face of any degree of flexion, so that the potential problem of intermittent contact between bus bar 315 and heating element 310 (that could arise for the embodiment shown in FIG. 2B, where bus bar 315 is in physical contact with heating element 310) can be avoided. The stitches are the only electrical connection between bus bar 315 and heating element 310, but, since the conductive thread has a much lower electrical resistance than the conductive fabric of heating element 310, the thread does not heat under normal conditions.

In addition to heating blanket applications described herein, such a design for providing for a uniform and stable conductive interface between a bus bar and a conductive fabric heating element material can be used in other applications. For example, such a design can improve the conductive interface between a bus bar or electrode and a conductive fabric in non-flexible heating elements, in electronic shielding, in radar shielding and other applications of conductive fabrics.

In some preferred embodiments, coupling 345 includes two or more rows of stitches for added security and stability. However, due to the flexible nature of blanket subassembly 300, the thread of stitched couplings 345 may undergo significant stresses. These stresses, over time and with multiple uses of a blanket containing subassembly 300, could lead to one or more fractures along the length of stitched coupling 345. Such a fracture, in other designs, could also result in intermittent contact points, between bus bar 315 and heating element 310, that could lead to a thermal breakdown of heating element 310 along bus bar. But, if such a fracture were to occur in the embodiment of FIG. 2B, insulating member 318 may prevent a thermal breakdown of heating element 310, so that only the conductive thread of stitched coupling 345 melts down along bus bar 315. According to some preferred embodiments, more than two rows of stitches are applied to each bus bar 315 for added safety and stability of the bus bar/heating element interface.

Alternative threads or yarns employed by embodiments of the present invention may be made of other polymeric or natural fibers coated with other electrically conductive materials. In addition, nickel, gold, platinum and various conductive polymers can be used to make conductive threads. Metal threads such as stainless steel, copper or nickel could also be used for this application.

According to an exemplary embodiment, bars 315 are comprised of flattened tubes of braided wires, such as are known to those skilled in the art (e.g., a flat braided silver coated copper wire) and may thus accommodate the thread extending therethrough, passing through openings between the braided wires thereof. In addition such bars are flexible to enhance the flexibility of blanket subassembly 300. According to alternate embodiments, bus bars 315 can be a conductive foil or wire, flattened braided wires not formed in tubes, an embroidery of conductive thread, or a printing of conductive ink. Preferably, bus bars 315 are each a flat braided silver-coated copper wire material, since a silver coating has shown superior durability with repeated flexion, as compared to tin-coated wire, for example, and may be less susceptible to oxidative interaction with a polypyrrole coating of heating element 310 according to an embodiment described below. Additionally, an oxidative potential, related to dissimilar metals in contact with one another is reduced if a silver-coated thread is used for stitched coupling 345 of a silver-coated bus bar 315.

According to an exemplary embodiment, a conductive fabric comprising heating element 310 comprises a non-woven polyester having a basis weight of approximately 170 g/m2 and being 100% coated with polypyrrole (available from Eeonyx Inc., Pinole, Calif.). The coated fabric has an average resistance (e.g., determined with a four point probe measurement) of approximately 15 ohms per square inch. This average resistance is suitable to produce the preferred watt density of 0.2 to 0.4 watts/sq. in. for surface areas of heating element 310 having a width, between bus bars 315, in the neighborhood of about 19 to 28 inches, when powered at about 48 volts. In some embodiments, the basis weight of the non-woven polyester may be chosen in the range of approximately 80-180 g/m2. However, other basis weights may be engineered to operate adequately are therefore within the scope of embodiments of the invention.

A resistance of such a conductive fabric may be tailored for different widths between bus bars (wider requiring a lower resistance and narrower requiring a higher resistance) by increasing or decreasing a surface area of the fabric that can receive the conductive coating. In some instances, this can be achieved by increasing or decreasing the basis weight of the nonwoven. Resistance over the surface area of the conductive fabrics is generally uniform in many embodiments of the present invention. However, the resistance over different portions of the surface area of conductive fabrics such as these may vary (e.g., due to (a) variation in a thickness of a conductive coating, (b) variation within the conductive coating itself, (c) variation in effective surface area of the substrate which is available to receive the conductive coating, or (d) variation in the density of the substrate itself). Local surface resistance across a heating element, for example heating element 310, is directly related to heat generation according to the following relationship:

$$Q(\text{Joules}) = I^2(\text{Amps}) \times R(\text{Ohms})$$

Variability in resistance thus translates into variability in heat generation, which can ultimately manifest as a variation in temperature.

According to preferred embodiments of the present invention, which are employed to warm patients undergoing surgery, precise temperature control is desirable. Means for determining heating element temperatures, which average out temperature variability caused by resistance variability across a surface of the heating element, are described below in conjunction with FIG. 3A.

Referring again to FIGS. 2A-2B, the flexibility of blanket subassembly 300 can allow blanket subassembly 300 to conform to the contours of a body (e.g., all or a portion of a patient undergoing surgery). This flexibility can be provided primarily by flexible heating element 310 and can be optionally enhanced by the incorporation of flexible bus bars. Conforming to the contours of a patient's body is preferable to simply bridging across high spots of the body. Such conformance may optimize a conductive heat transfer from heating element 310 to a surface of the body.

The uniform watt-density output across the surface areas of preferred embodiments of heating element 310 translates into generally uniform heating of the surface areas, but not necessarily a uniform temperature. For example, at locations of heating element 310 which are in conductive contact with a body acting as a heat sink, the heat is efficiently drawn away from heating element 310 and into the body (e.g., by blood flow). At the same time, at those locations where heating element 310 does not come into conductive contact with the body, an insulating air gap exists between the body and those portions, so that the heat is not drawn off those portions as easily. Therefore, those portions of heating element 310 not in conductive contact with the body will gain in temperature, since heat is not transferred as efficiently from these portions as from those in conductive contact with the body. The 'non-contacting' portions will reach a higher equilibrium temperature than that of the 'contacting' portions, when the radiant and convective heat loss equal the constant heat production through heating element 310. Since the heat generation is generally uniform, the heat flux to the patient will also be generally uniform. However, at the non-contacting locations, the temperature is higher to achieve the same flux as the contacting portions. Some of the extra heat from the higher temperatures at the non-contacting portions can therefore be dissipated out the back of the pad instead of into the patient.

Although radiant and convective heat transfer are more efficient at higher heater temperatures, the laws of thermodynamics dictate that as long as there is a uniform watt-density of heat production, even at the higher temperature, the radiant and convective heat transfer from a blanket of this construction will result in a generally uniform heat flux from the blanket. Therefore, by controlling the 'contacting' portions to a safe temperature (e.g., via a temperature sensor assembly 321 coupled to heating element 310 in a location where heating element 310 will be in conductive contact with the body), the 'non-contacting' portions, will also be operating at a safe temperature because of the less efficient radiant and convective heat transfer.

According to preferred embodiments, heating element 310 comprises a conductive fabric having a relatively small thermal mass. When a portion of such a heating element that is operating at the higher temperature is touched, suddenly converting a 'non-contacting' portion into a 'contacting' portion, that portion will cool almost instantly to the lower operating temperature.

Figure 3A:
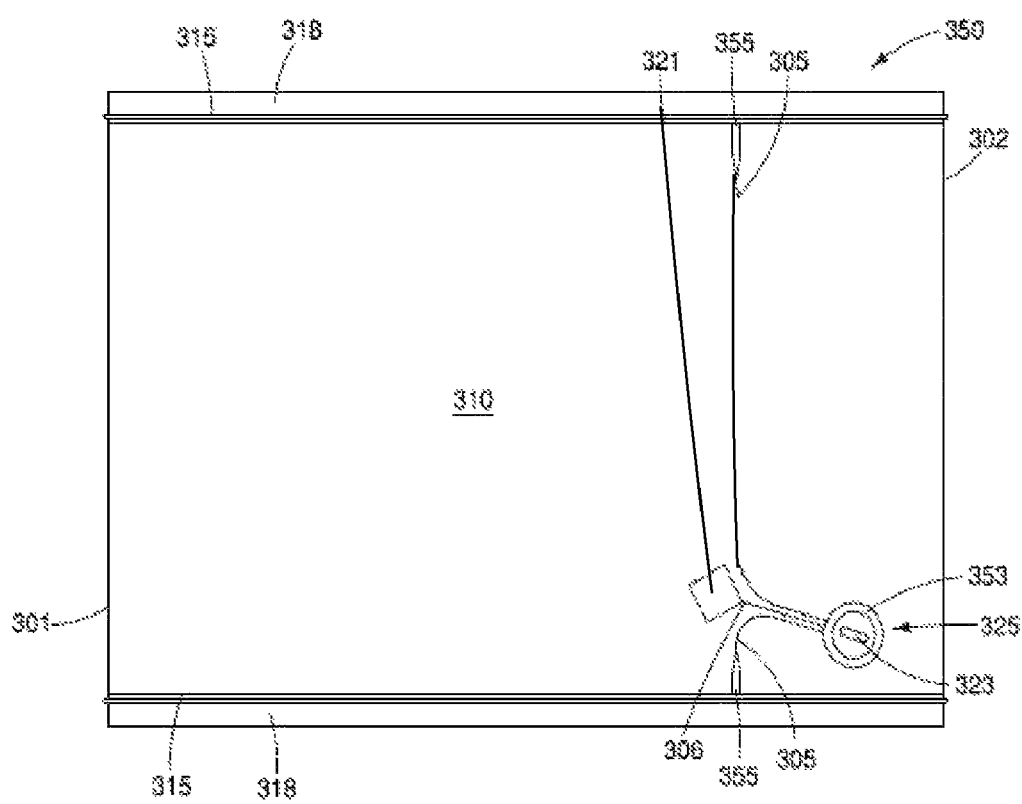
FIG. 3A is a top plan view of a heating element assembly, according to some embodiments of the present invention, which may be incorporated in the blanket shown in FIG. 1.
Figure 3B:
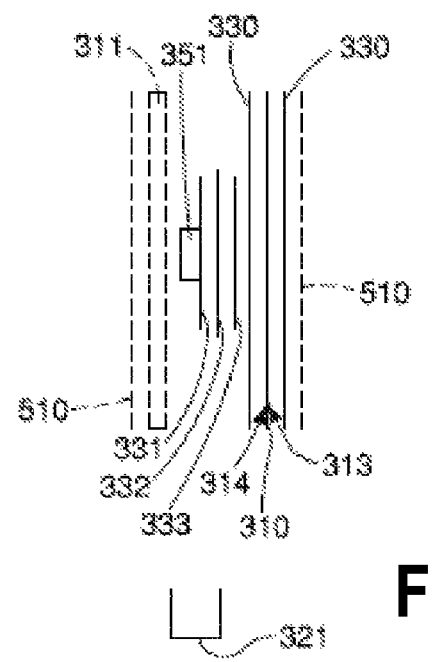
FIG. 3B is a section view of the temperature sensor assembly of FIG. 3A.

FIGS. 3A-3B show a heating element assembly 350 similar to the heating element assembly 350 of FIG. 1. Referring again to FIGS. 3A-3B, the heating element assembly can include a temperature sensor assembly 321. As shown, the temperature sensor assembly 321 is coupled to heating element 310 at a location where heating element 310 would come into conductive contact with the patient. This can assist in maintaining a safe temperature distribution across heating element 310. The more constant the temperature information, the more the temperature controller can rely on it in controlling the heater temperature. In some embodiments, the temperature sensor assembly 321 can even be provided separately from the heating blanket.

According to embodiments of the present invention, zones of heating element 310 may be differentiated according to whether or not portions of heating element 310 are in conductive contact with a body (e.g., a patient undergoing surgery). In some embodiments, the threshold temperature is between 37 and 43° C. In one particular embodiment, the threshold temperature is 43° C. A temperature of 43° C. has been shown to provide beneficial warming to a patient without providing excessive heat. In the case of conductive heating, gentle external pressure may be applied to a heating blanket including heating element 310. Such pressure conforms heating element 310 into better conductive contact with the patient to improve heat transfer. However, if excessive pressure is applied, the blood flow to that skin may be reduced at the same time that the heat transfer is improved and this combination of heat and pressure to the skin can be dangerous. It is well known that patients with poor perfusion should not have prolonged contact with temperatures in excess of approximately 42° C. Several studies show 42° C. to be the highest skin temperature that cannot cause thermal damage to normally perfused skin, even with prolonged exposure. (Stoll & Greene, Relationship Between Pain and Tissue Damage Due to Thermal Radiation. J. Applied Physiology 14(3):373-382. 1959; and Moritz and Henriques, Studies of Thermal Injury: The Relative Importance of Time and Surface Temperature in the Causation of Cutaneous Burns. Am. J. Pathology 23:695-720, 1947). Thus, according to certain embodiments of the present invention, the portion of heating element 310 that is in conductive contact with the patient is controlled to approximately 43° C. in order to achieve a temperature of about 41-42° C. on a surface of a heating blanket cover that surrounds heating element 310 (e.g., shell 105 of FIG. 1).

FIG. 3B illustrates the temperature sensor assembly 321 assembled on side 314 of the heating element 310. As shown, the heating element 310 is overlaid on both sides 313, 314 with an electrically insulating layer 330. The electrically insulating layer 330 is preferably formed of a flexible non-woven very low loft fibrous material (e.g., 1.5 ounces-per-square-yard nylon), which is preferably laminated to sides 313, 314 with a hotmelt laminating adhesive. In some embodiments, the adhesive is applied over the entire interfaces between insulating layer 330 and heating element 310. Other examples of suitable materials for insulating layer 330 include, without limitation, polymeric foam, a woven fabric, such as cotton or fiberglass, and a relatively thin plastic film, cotton, and a non-flammable material, such as fiberglass or treated cotton. According to preferred embodiments, overlaid insulating layers 330 prevent electrical shorting of one portion of heating element 310 with another portion of heating element 310 if heating element 310 is folded over onto itself. Many such embodiments prevent electrical shorting without compromising the flexibility of heating assembly 350. Heating element assembly 350 may be powered by a relatively low voltage (approximately 48V). Insulating layers 330 may even be porous in nature to further maintain the desired flexibility of assembly 350.

As shown in FIG. 3A, an assembly of leads 305, 306 and junctions 355 can connect the bus bars 315 and the temperature sensor assembly 321 to an electrical connector housing 325. Leads 305 couple the connector housing 325 to bus bars 315 at junctions 355. Lead 306 couples the temperature sensor assembly 321 to the connector housing 325. In many embodiments, leads 305, 306 extend over any insulating layer (e.g., 330 in FIG. 3B) and into the electrical connector housing 325. As is noted above (see discussion in connection with FIG. 1) and discussed in greater detail below (see discussion in connection with FIG. 4A), electrical connector housing 325 can contain a connector plug 323.

Returning now to FIG. 3B, the illustrative temperature sensor assembly 321 will be described in greater detail. The temperature sensor assembly 321 can include a temperature sensor 351 (e.g., a surface mount chip thermistor (such as a Panasonic ERT-J1VG103FA: 10K, 1% chip thermistor)) soldered to an etched metal foil. In many embodiments, a substrate 331 (e.g., of polyimide (Kapton)) surrounds the temperature sensor 351. A heat spreader 332 (e.g., a copper or aluminum foil) can be mounted to an opposite side of substrate 331 (e.g., being bonded with a pressure sensitive adhesive). Substrate 331 can be relatively thin (e.g., about 0.0005-inch thick) so that heat transfer between heat spreader 332 and sensor is not significantly impeded.

In some embodiments, the temperature sensor 351 is positioned such that the regions surrounding sensor 351 will be in conductive contact with the body when a heating blanket is placed over a body. As previously described, in many instances, it is desirable that a temperature of approximately 43° C. be maintained over a surface of heating element 310 which is in conductive contact with a body of a patient undergoing surgery. An additional alternate embodiment is contemplated in which an array of temperature sensors are positioned over the surface of heating element 310, being spaced apart to collect temperature readings. In some such embodiments, the collected temperatures can be averaged to account for resistance variance.

Figure 4A:
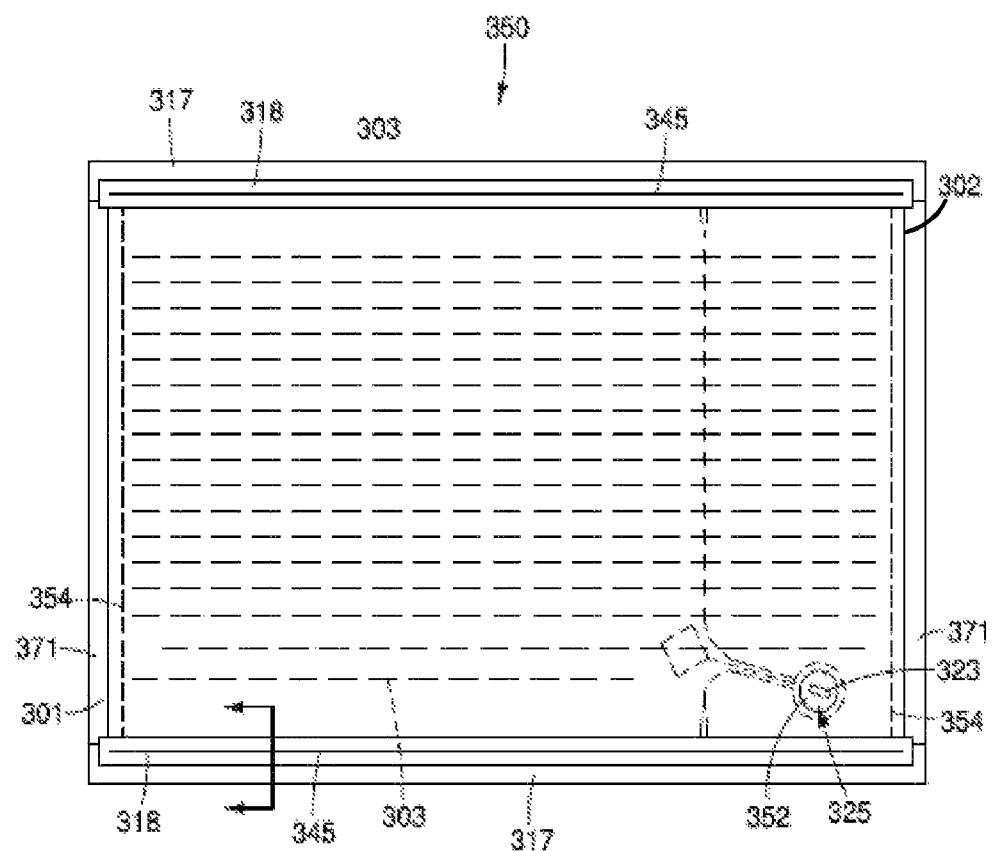
FIG. 4A is a top plan view of a heating element assembly, which may be incorporated in the blanket shown in FIG. 1.
Figure 4B:
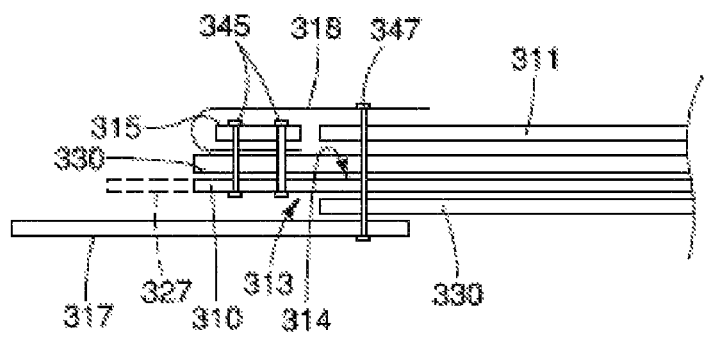
FIG. 4B is a cross-section view through section line 4B-4B of FIG. 4A.

FIGS. 4A-4B show a heating element assembly 350 that may be incorporated into a heating blanket (e.g., heating blanket 100 of FIG. 1). As shown, the heating element assembly 350 includes heating element 310 overlaid with electrical insulation 330 on both sides 313, 314 and thermal insulation layer 311 extending over the top side 314 thereof (dashed lines show leads and sensor assembly beneath layer 311).

A heating blanket may include a layer of thermal insulation 311 extending over a top side (corresponding to side 314 of heating element 310 as shown in FIG. 2B) of heating assembly 350 as discussed above. According to the illustrated embodiment, layer 311 is inserted beneath a portion of each insulating member 318. The insulating members 318 have been folded over the respective bus bar 315 (e.g., as illustrated by arrow B in FIG. 2B), and then held in place by a respective row of non-conductive stitching 347 that extends through insulating member 318, layer 311 and heating element 310. Although not shown, it should be appreciated that layer 311 may further extend over bus bars 315. Although insulating layer 330 is shown extending beneath layer 311 on side 314 of heating element 310, according to alternate embodiments, layer 311 independently performs as a thermal and electrical insulation so that insulating layer 330 is not required on side 314 of heating element 310. FIG. 4A further illustrates, with longitudinally extending dashed lines, a plurality of optional slits 303 in layer 311, which may extend partially or completely through layer 311, in order to increase the flexibility of assembly 350. Such slits are desirable if a thickness or density of layer 311 is such that it prevents the heating blanket from draping effectively about a patient. The optional slits are preferably formed, for example, extending only partially through layer 311 starting from an upper surface thereof, to allow bending of the heating blanket about a patient and to prevent bending of the heating blanket in the opposition direction.

Returning now to FIG. 3A, to be referenced in conjunction with FIGS. 1 and 4A, connector housing 325 and connector plug 323 will be described in greater detail. According to certain embodiments, housing 325 is an injection molded thermoplastic (e.g., PVC) and may be coupled to assembly 350 by being stitched into place, over insulating layer 330. FIG. 3A shows housing 325 including a flange 353 through which such stitching can extend.

Referring to FIGS. 1 and 4A, in some embodiments, a surface of flange 353 of housing 325 protrudes through a hole formed in thermal insulating layer 311 so that a seal may be formed (e.g., by adhesive bonding and/or welding, such as heat sealing) between an inner surface of shell 105 and surface 352. According to one embodiment, wherein housing 325 is injection molded PVC and the inner surface of shell 105 is likewise PVC, housing 325 is sealed to shell 105 via a solvent bond. It may be appreciated that the location of the connector plug 323 is suitable to keep the corresponding connector cord well away from the surgical field. In embodiments in which the inner surface of shell 105 is coated with polyurethane and the housing 325 is injection molded PVC, an intermediate adhesive can be used to allow for a heat seal connection (e.g., a solvent bond adhesive can be applied to the housing 325, and the polyurethane film can be heat sealed to the exposed adhesive).

FIGS. 4A-4B further illustrate a pair of securing strips 317, each extending laterally from and alongside respective lateral portions of heating element 310, parallel to bus bars 315, and each coupled to side 313 of heating element 310 by the respective row of non-conductive stitching 347. Another pair of securing strips 371 is shown in FIG. 4A, each strip 371 extending longitudinally from and alongside respective side edges 301, 302 of heating element 310 and being coupled thereto by a respective row of non-conductive stitching 354. Strips 371 may extend over layer 311 or beneath heating element 310. As shown, strips 317 preferably extend over conductive stitching of stitched coupling 345 on side 313 of heating element 310. The strips 317 can provide a layer of insulation that can prevent shorting between portions of side 313 of heating element 310 if heating element 310 were to fold over on itself along rows of conductive stitching of stitched coupling 345 that couple bus bars 315 to heating element 310. In some embodiments, strips 317 may alternately extend over insulating member 318 on the opposite side of heating element 310. According to the illustrated embodiment, securing strips 317 and 371 are made of a polymer material (e.g., PVC). They may be heat sealed between the sheets of shell (105 of FIG. 1) in corresponding areas of the heat seal zone in order to secure heating element assembly 350 within a corresponding gap between the two sheets of shell (105 of FIG. 1). According to an alternate embodiment, for example, shown by dashed lines in FIGS. 2A and 4B, heating element 310 extends laterally out from each bus bar 315 to a securing edge 327, which may include one or more slots or holes 307 extending therethrough so that inner surfaces of sheets of shell (105 of FIG. 1) can contact one another to be sealed together and thereby hold edges 327.

Referring to FIG. 1, connector plug 323 can protrude from shell 105 of the heating blanket 100. An extension cable may couple the heating element assembly 350 to a console 60. The console 60 includes a shut-off timer 30 and a power source 50 each coupled to a control system (or controller) 40. The shut-off timer 30 can be operatively coupled to the control system 40, meaning that the shut-off timer 30 can be integrated into the control system 40, the shut-off timer 30 can be a separate component, or the shut-off timer 30 and the control system 40 can have any other suitable functional relationship. The temperature sensor assembly 321 can be configured to provide temperature information to the control system 40, which may act as a temperature controller. The controller may function to interrupt such power supply (e.g., in an over-temperature condition) or to modify the duty cycle to control the heating element temperature.

The power source 50 and power type can be any type known in the art. In certain embodiments, the power source 50 supplies a straight-line DC voltage to the control system 40, and the control system 40 provides a pulse-width-modulated voltage (e.g., at a 75% duty cycle) to the heating element assembly 350. Of course, other duty cycles and/or voltage levels can be used based on the design of the blanket and its heating element in order to achieve a desired threshold temperature in a reasonable amount of time. Too high of voltage or duty cycle, while decreasing the time to reach the desired temperature threshold, may increase the amount of temperature overshoot before the control system reduces or shuts off power. Moreover, in the case of temperature sensor failure, thermal runaway presents a greater concern with relatively higher voltage or duty cycle settings. Too low of a voltage or duty cycle may cause unreasonably long warm-up times.

As discussed above, warming blankets in accordance with embodiments of the invention include or make use of a shell or covering, such as shell 105 shown in FIG. 1. Several embodiments of such shells will now be described in greater detail, although it should be understood that these embodiments are for illustrative purposes only.

Figure 5A:
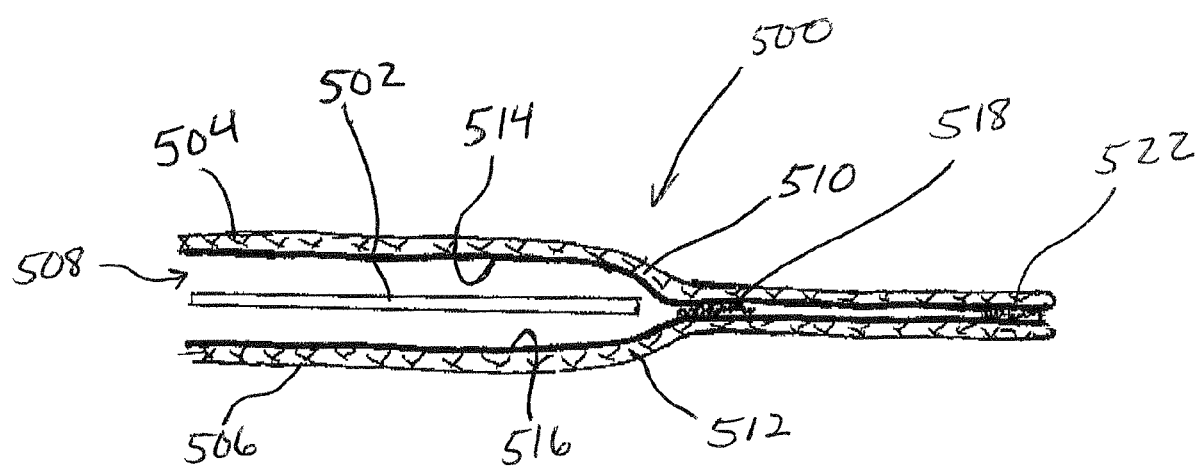
FIG. 5A is a cross-section of a shell containing a heating element according to some embodiments of the present invention.

FIG. 5A is a cross-section of a shell 500 containing a heating element 502 in accordance with some embodiments of the invention. The shell 500 can include a top sheet 504 and a bottom sheet 506 that are welded or coupled at one or more locations in order to define a pocket or pouch 508 that can enclose the heating element 502. Any type of suitable weld may be used, such as heat welding (heat bonding), RF welding, ultrasonic welding, etc., depending on the type of materials used in sheets 504, 506. Each sheet 504 and 506 can comprise a flexible, substantially water-resistant material and include the ability to be welded together. In some embodiments, the water-resistant material includes a single layer, and in some embodiments, sheets are comprised of a laminate of two or more layers. For instance, in some embodiments one or both of sheets 504, 506 are comprised of a single layer of polyvinyl chloride (PVC). In such embodiments where PVC is used, high frequency or RF welding (RF heat sealing) may be used to bond the sheets 504, 506 together. PVC sheets also provide a water-resistant material in order to protect the heating element 502 from fluids to which the heating blanket is exposed.

In some embodiments, one or both of sheets 504, 506 include respective strengthening layers 510, 512 that provide strength and color to the shell 500. For example, the strengthening layers 510, 512 can be a fibrous material such as woven nylon. It will be appreciated that other materials can also be used for this layer.

With further reference to FIG. 5A, sheets 504, 506 can each also include a second layer 514, 516 located along an inside surface of the sheets 504, 506. These second layers can in some embodiments provide a water-resistant layer in order to protect the heating element 502 from fluids to which the heating blanket is exposed. For example, the second layers 514, 516 can be a polymeric film attached to the strengthening layer. In some embodiments, the second layers 514, 516 are preferably polymeric film layers that are a durable and made of a weldable material, such as urethane or vinyl, which can be laminated or extrusion coated on to the strengthening layers 510, 512 and the second layers 514, 516 may be welded together via heating bonding along the bonding points.

In some embodiments, one or both of sheets 504, 506 include a third layer laminated to their respective outer surfaces. The third layer, in some embodiments, is a polymeric layer, which may or may not be the same material as second layers 514, 516 in some embodiments. For example, the third layer can comprise a polymeric layer that can substantially seal one or both of the strengthening layers so that it cannot be substantially wetted. In some embodiments, the third layer may also be somewhat tacky so that it prevents the blanket from slipping when applied over a patient. The third layer may also comprise a material with the ability to limit and/or prevent iodine and cleaning solutions from staining the blanket. Examples of materials that could serve this purpose include vinyl and silicone.

With further reference to FIG. 5A, top sheet 504 and bottom sheet 506 can be positioned on opposing sides of heating element 502 to envelope the heating element. Although descriptive terms "top" and "bottom" are used herein, it will be appreciated that in some embodiments, the sheets 504 and 506 may be identical and that either sheet may be referred to as "top" or "bottom." As shown in the embodiment of FIG. 5A, the sheets are positioned so that the weldable layers 514, 516 of each sheet oppose each other.

Figure 5B:
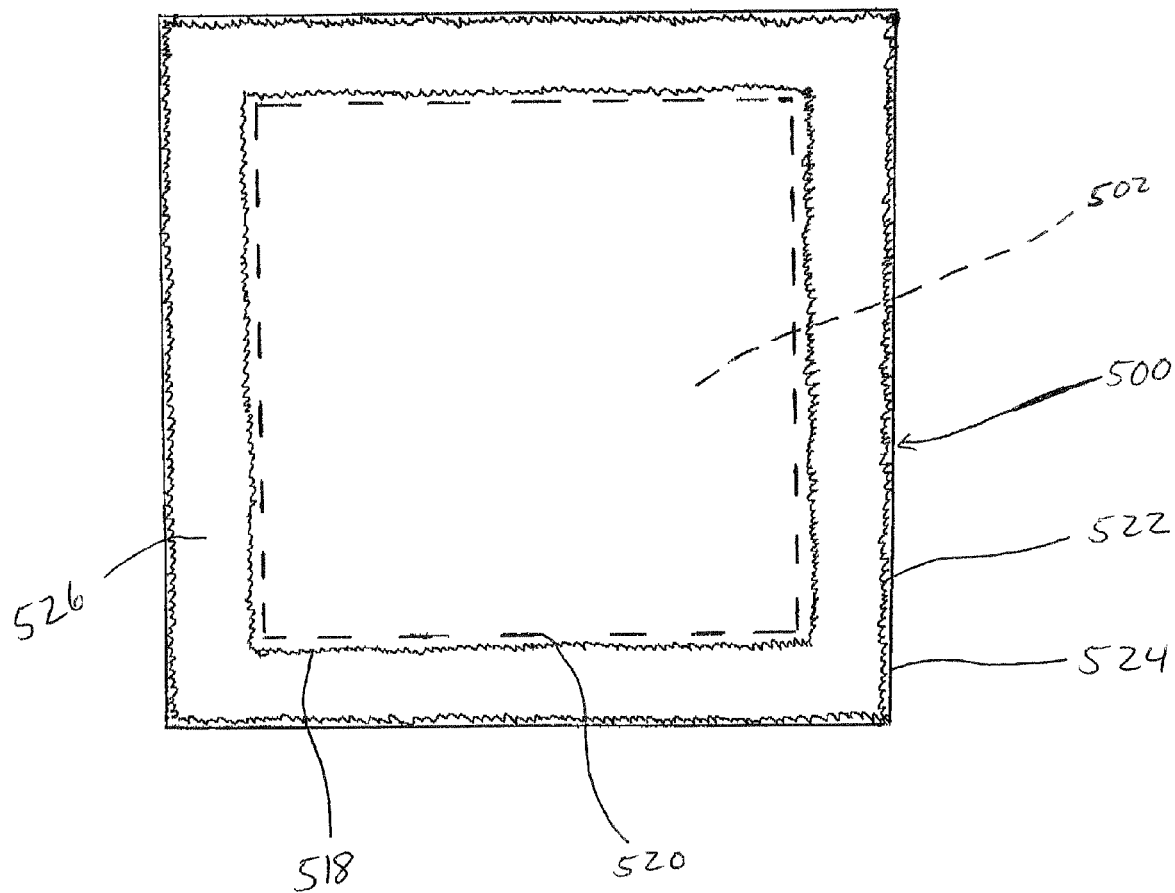
FIG. 5B is a top plan view of the shell of FIG. 5A.

FIG. 5B is a top plan view of the heating blanket depicted in FIG. 5A. In some embodiments, the sheets 504, 506 are sized to completely cover the heating element 502, and can extend beyond all edges (e.g., top, bottom, right and left side edges in FIG. 5B) of the heating element 502. In some embodiments, the heating element 502 is substantially hermetically sealed into the shell 500 formed by the two sheets 504, 506. As shown in the embodiment of FIGS. 5A and 5B, the sheets 504, 506 are coupled together along two welds. A first weld 518 can extend about a perimeter 520 of the heating element 502, thus surrounding the entire periphery of the heating element. A second weld 522 can extend about a perimeter edge 524 of the sheets 504, 506, thus sealing the periphery of the sheets together. In some embodiments, the space 526 between the first weld 518 and the second weld 522 may be totally or partially welded together. In alternate embodiments, the space 526 between the welds may contain other structural components of the blanket as previously described and further discussed below. For example, the space 526 can enclose weighting members, the added weight of which helps retain the blanket in position and against the patient.

The weld used in some embodiments to create a substantially hermetically sealed shell for protecting the heating element provides a number of advantages over traditional bonding mechanisms such as sewing, stitches, rivets or grommets that create or reinforce a seal. In certain embodiments of those that employ a heat sealed shell, the external surface of the substantially hermetically sealed shell is not punctured by needle holes, sewing, stitching, rivets, grommets or other fasteners. These traditional fasteners create holes and can accumulate contaminants from blood and body fluids. These holes, crevasses, and fibrous materials such as thread are difficult or even impossible to clean with standard cleaning methods and solutions. Exemplary heating blankets described herein can advantageously have a smooth, non-violated shell, without external attachments or physical places to trap contaminants, thus providing a readily and thoroughly cleanable heating blanket in some embodiments. As will be appreciated, the welded construction used in some embodiments can also facilitate a variety of features that would otherwise require traditional fasteners such as sewing, stitching, riveting, grommets or snaps.

Figure 6:
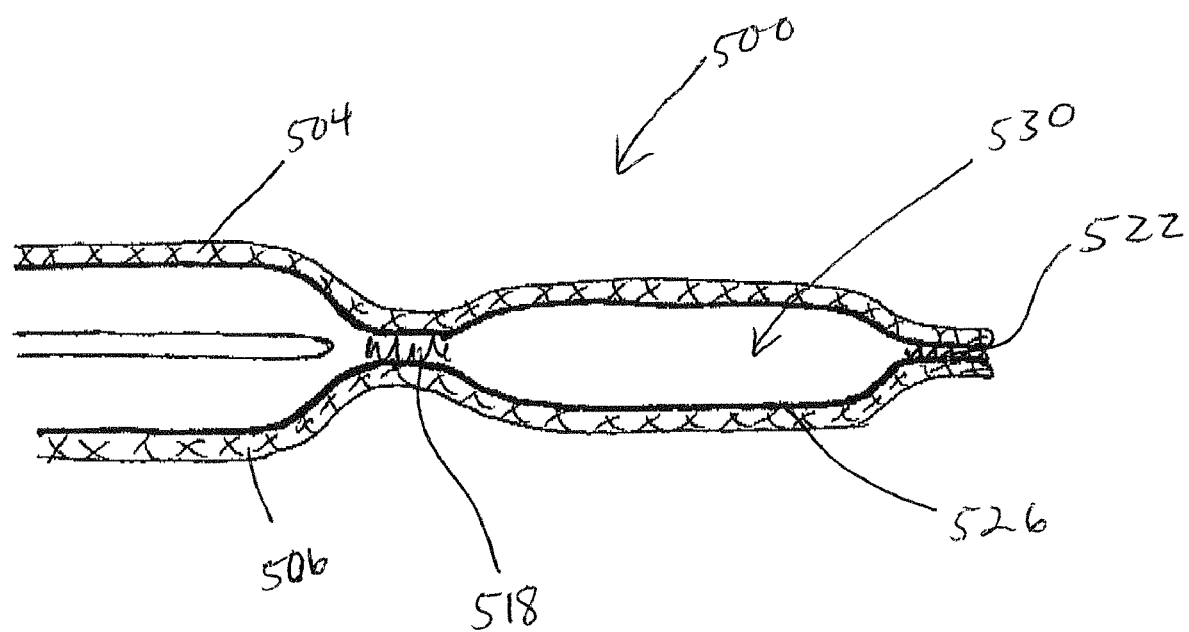
FIG. 6 is a cross-section of a shell containing an air pocket according to some embodiments of the present invention.

In some embodiments, portions of the shell extending beyond the perimeter of the heating element can form non-heated edge flaps of the heating blanket, such as those described above. Exemplary non-heated edge flaps can preferably extend from 1 inch to 24 inches away from the perimeter of the heating element, although it will be appreciated that any suitable length of extension is possible. The non-heated edge flaps can be used to create a cocoon-like space that traps the heat from the heater in a space around the patient. For example, in alternative embodiments, the edges 112, 114, 116, and 118 of the heating blanket depicted in FIG. 1 can include non-heated edge flaps instead of lateral portions of the heating element. The non-heated edge flaps can thus create a thermal barrier between the heater edge and the operating table or bed. In some embodiments, the two sheets of the non-heated edge flaps may be partially or completely welded together between the first weld about the perimeter of the heating element and the second weld about the perimeter of the warming blanket. With reference to FIG. 6, in embodiments with a partial weld, the non-welded area may include an air pocket 530. Air can be introduced into the space 526 between the first weld 518 and the second weld 522. Embodiments with such an air pocket 530 can thus provide a thermal barrier that further limits the escape of heat from the space around the patient.

Figure 7A:
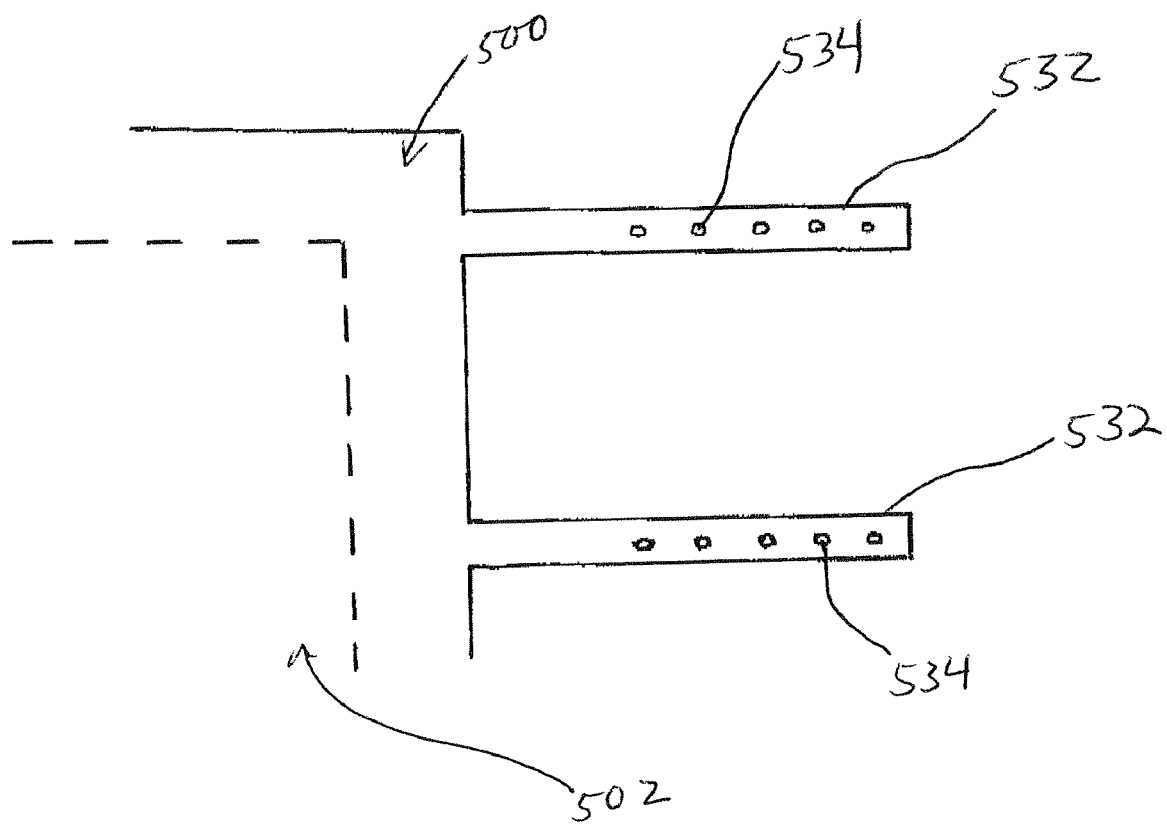
FIG. 7A is a top plan view of a shell having straps according to some embodiments of the present invention.
Figure 7B:
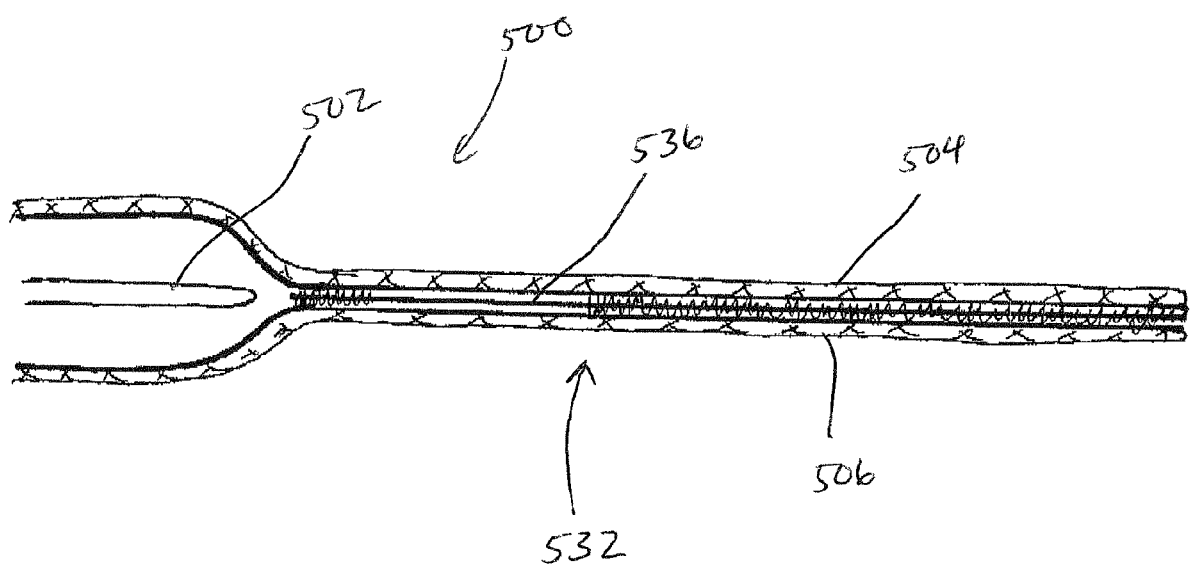
FIG. 7B is a cross-section of the shell of FIG. 7A.

With reference to FIG. 7A, some exemplary heating blankets can include one or more straps 532 extending from the blanket for securing the blanket in place over the patient. In some embodiments, the straps 532 are preferably of the same material and contiguous with the sheets making up the shell and protrude from the edges of the sheets such that there is no seam joining the straps 532 with the sheets. In some embodiments, holes 534 can be punched in the straps 532 to facilitate buckling the straps (e.g., to another blanket strap extending from a different edge of the blanket, to a protuberance extending from the blanket, etc.), hanging the warming blanket, or other common uses. With reference to FIG. 7B, some embodiments can include a reinforcing layer 536 positioned between the sheets 504, 506 before they are welded in order to reinforce the straps 532. For example, the reinforcing layer can in some embodiments comprise a plastic film such as a urethane film. The reinforcing layer may be formed in addition to strengthening layer of sheets 504, 506 described above. Alternatively, the reinforcing layer could be formed by the inclusion of the strengthening layer on one or both of sheets 504, 506 at the strap locations shown in FIG. 7A. As will be appreciated, the straps 532 are provided with the warming blanket without the addition of sewing, stitching, grommets or other traditional fasteners, thus providing the advantages previously discussed.

Figure 8:
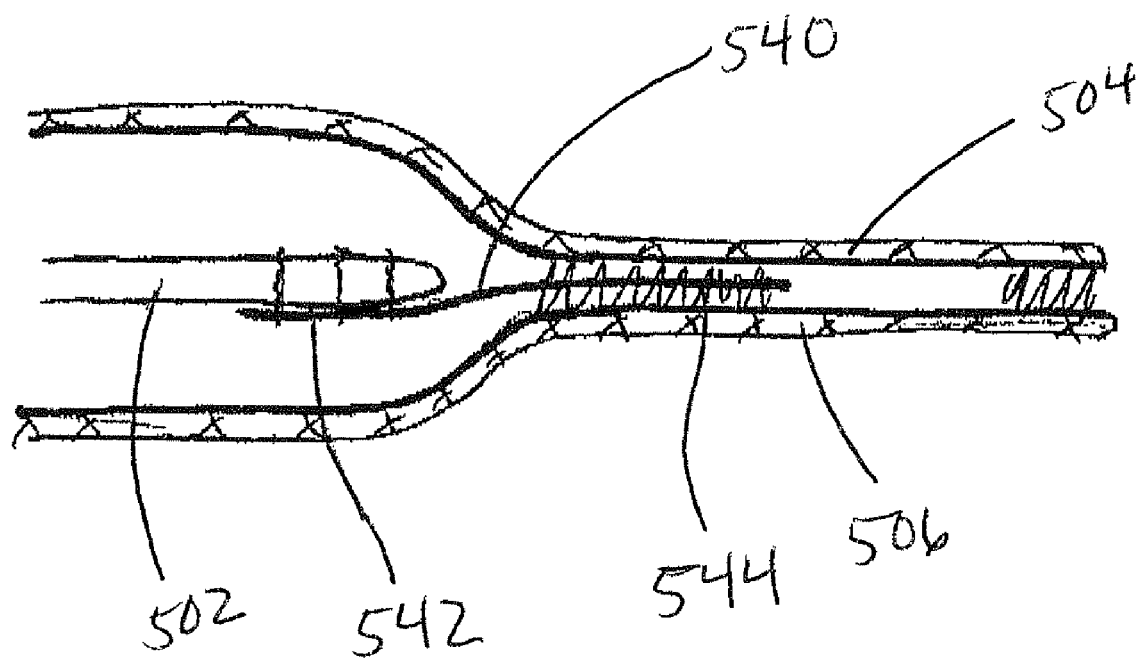
FIG. 8 is a cross-section of a shell containing a heating element secured to the shell according to some embodiments of the present invention.

As previously discussed with reference to at least FIGS. 2A, 4A and 4B, securing strips 317, 371 or securing edges 327 can be provided in some embodiments to facilitate securing the heating element to the shell. With reference to FIG. 8, an exemplary securing strip 540 can comprise a weldable plastic film, for example, a urethane film. A first end 542 of the securing strip 540 can be attached to the heating element 502, for example by sewing. A second end 544 of the securing strip 540 (or securing edge according to alternate embodiments) can be placed between the two sheets 504, 506 and incorporated into the welds between the two sheets. Thus the heater is held in an extended position within the shell, without using stitches, sewing, rivets or grommets that would pierce the flexible material sheets and make the shell difficult to clean.

Figure 9A:
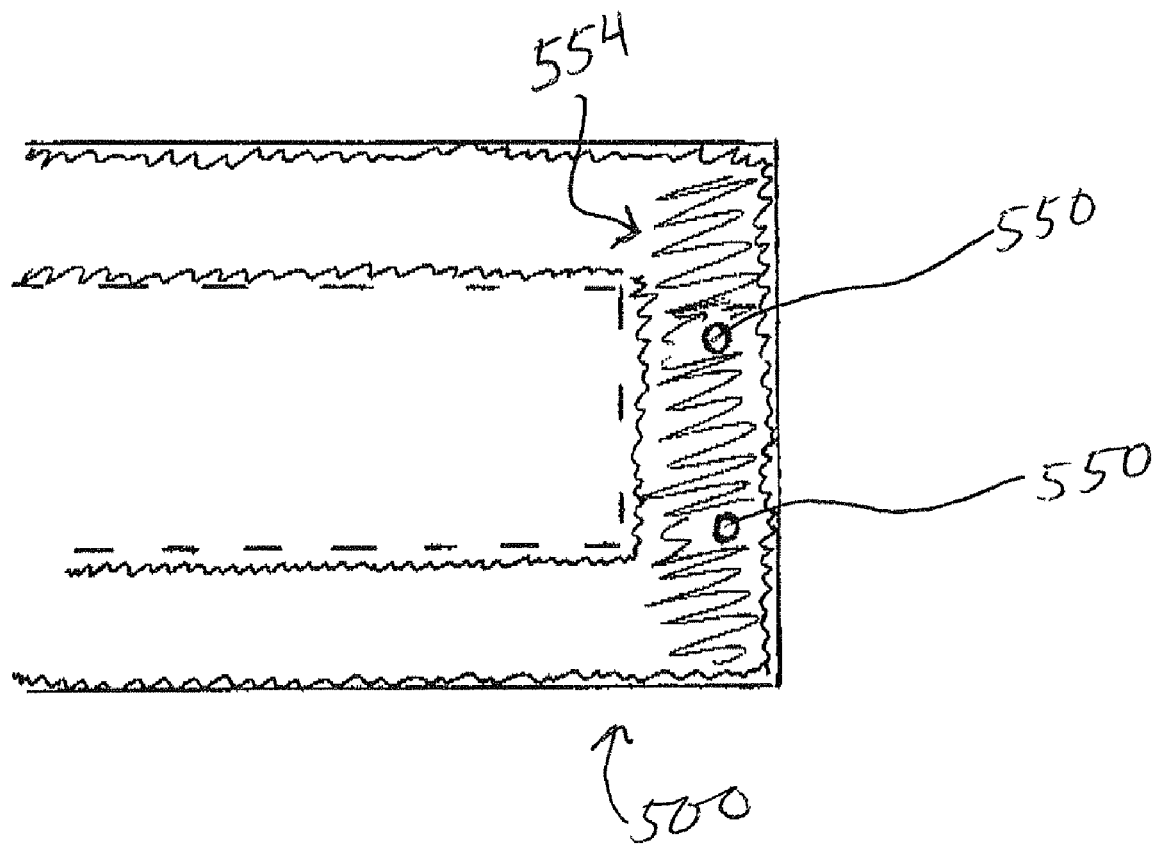
FIG. 9A is a top plan view of a shell containing reinforced hanger points according to some embodiments of the present invention.
Figure 9B:
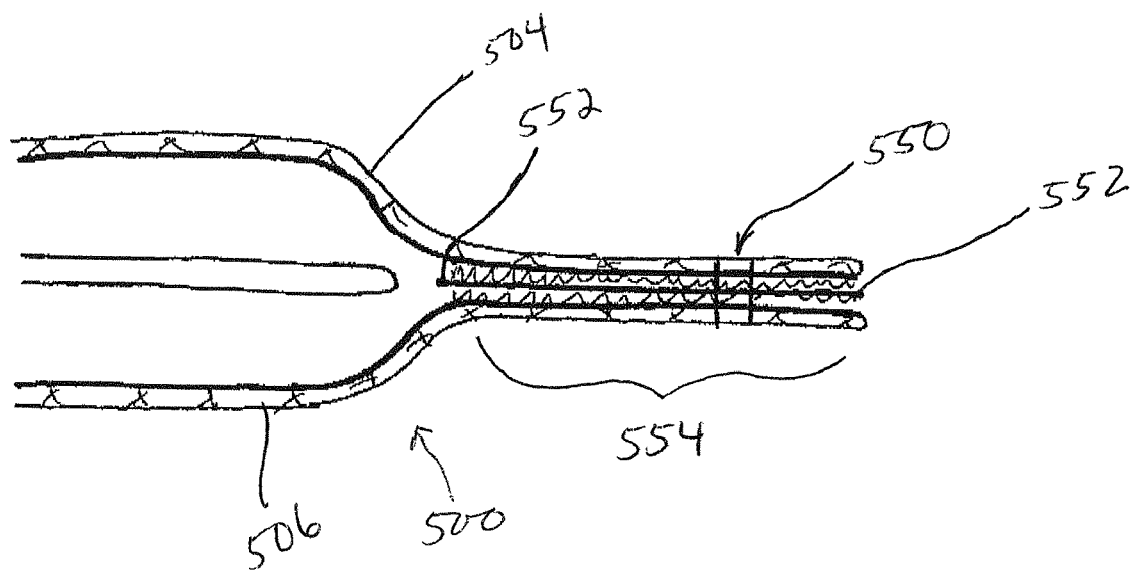
FIG. 9B is a cross-section of the shell of FIG. 9A.

With reference to FIGS. 9A-9B, some exemplary shells provide reinforced hanger points 550 without the use of grommets or another similar mechanism for reinforcement. As shown, a reinforcing layer 552 extends between the sheets 504, 506 where they are welded at one end about the perimeter of the heating element 502. The reinforcing layer 552 may be formed in addition to strengthening layer of sheets 504, 506. In some embodiments more than one reinforcing layer may be utilized, for example, on opposing ends of the shell 500 or one layer integrated into one of both of sheets 504, 506. The reinforcing layer 552 can in some embodiments comprise one or more pieces of thermally bondable plastic film, for example a urethane film. The reinforcing layer 552 is incorporated into a weld 554 that may extend from near the perimeter of the heater to near the perimeter of the sheets. One or more holes can be punched through both sheets and through the reinforcing layer 552 to create a hanging point 550. The exemplary reinforcing layer 552 reinforces the hanging point 550 without the need for additional grommets that would make the blanket more difficult to clean.

Figure 10A:
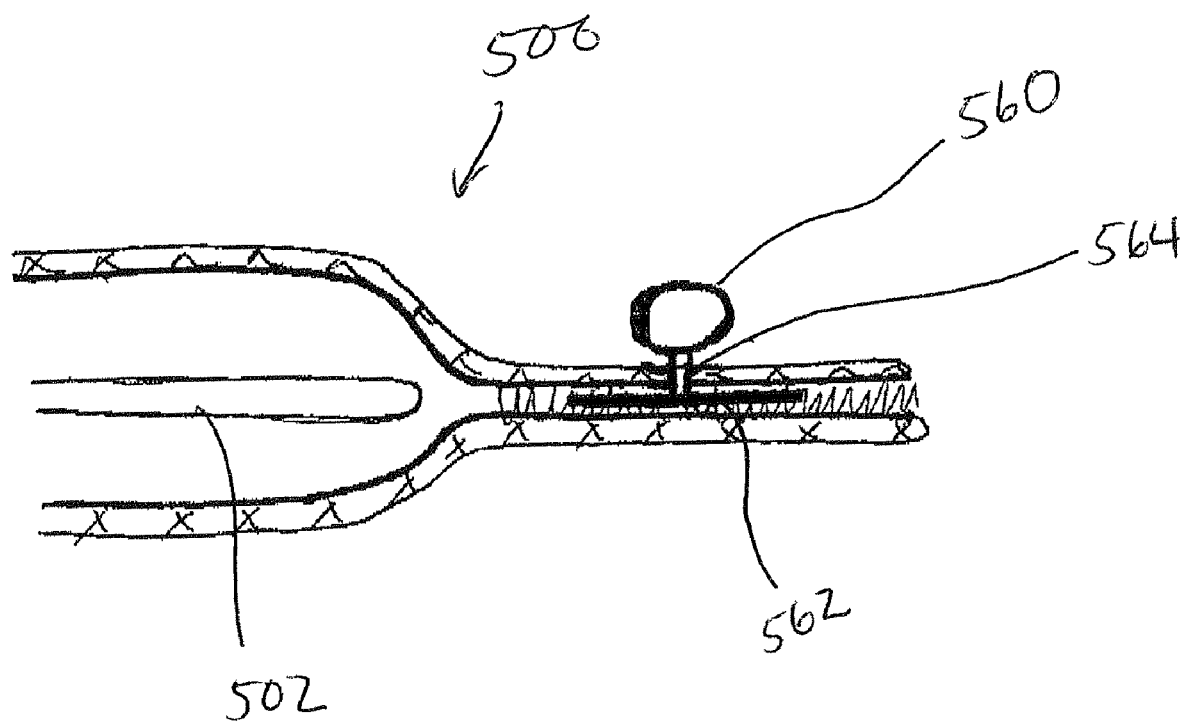
FIG. 10A is a cross-section of a shell containing a heating element, including an attachment point secured to the shell according to some embodiments of the present invention.
Figure 10B:
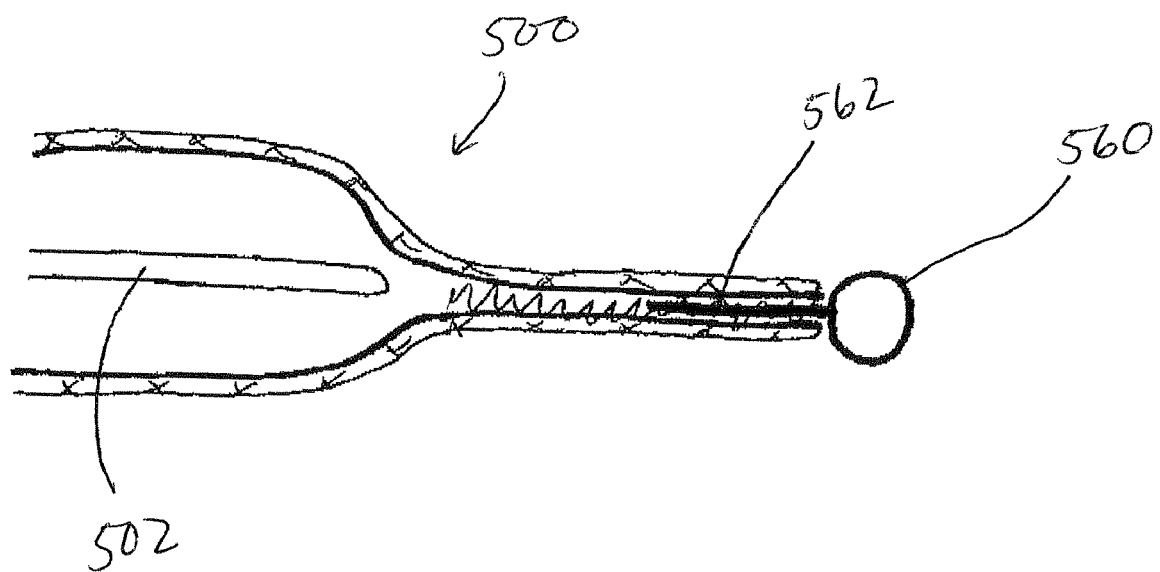
FIG. 10B is a cross-section of a shell containing a heating element, including an attachment point secured to the shell according to some embodiments of the present invention.

With reference to FIGS. 10A-10B, exemplary shells are shown with an incorporated anchor point 560. As shown, the anchor point 560 can in some embodiments be a "ball-shaped" or a "mushroom-shaped" protuberance which can serve as an attachment post on which a strap with holes in it may be secured, for example, the straps of FIGS. 7A-7B. The anchor point 560 can be made of plastic or some other material such as metal. As shown in FIGS. 10A-10B, the anchor point 560 can be molded or otherwise attached to an anchoring layer 562, which in some embodiments comprises a flat piece of thermally bondable plastic material, such as, for example, a urethane material. The anchoring layer 562 can be placed between the two sheets 504, 506 about the perimeter of the heating element 502 and the anchor point 560 can extend from the edges of the sheets as in FIG. 10B or through a hole 564 made in one of the sheets as in FIG. 10A. The sheets 504, 506 can be welded to the anchoring layer 562 to anchor the anchoring layer 562 between the sheets and also to seal the cut edge of the hole 564 or edge of the sheets.

In some embodiments, a piece of ribbing or piping can be molded to the edge of an anchoring layer similar to that shown in FIG. 10B. The anchoring layer can then be placed between the two sheets at their edges such that the ribbing or piping protrudes beyond the edges of the sheets. Exemplary ribbing or piping may be plastic or another suitable material such that the ribbing or piping advantageously seals the edges of the shell and creates a soft edge to the warming blanket. Portions of the ribbing or piping may include the anchor point 560.

Figure 11:
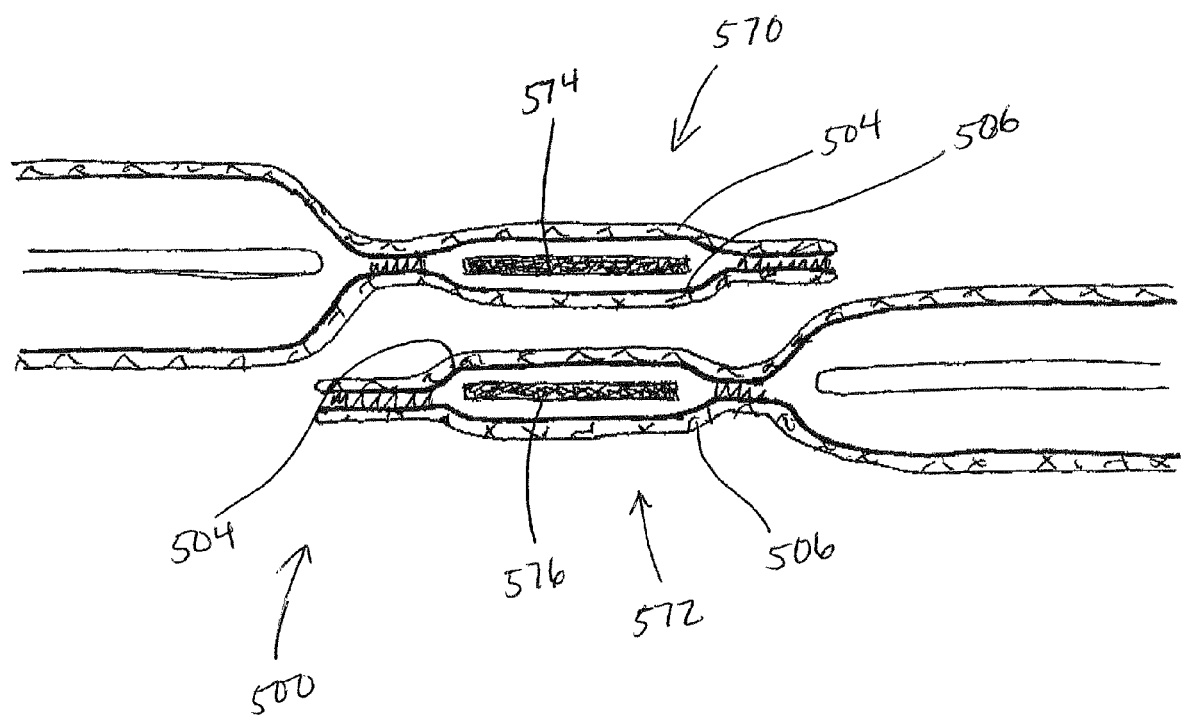
FIG. 11 is a cross-section of two ends of a shell containing a heating element, including a securing magnet.

With reference to FIG. 11, in some embodiments, a warming blanket can be secured to a patient with one or more magnets and/or ferrous metal pieces. FIG. 11 shows two opposing ends 570, 572 of a single shell 500 and warming blanket configured in a loop according to some embodiments. As shown, a magnet 574 can be fixed in position between sheets 504, 506 at end 570 via appropriately placed welds of sheets 504, 506. Alternately a ferrous metal piece 576 or another magnet can be fixed in position between sheets 506, 504 at end 572 in the same manner as magnet 574. The magnet 574 is placed in a position to mate with ferrous metal piece 576, securing the blanket in place. The metal piece 576 and the magnet 574 are both contained between the sheets and therefore do not complicate the cleaning of the warming blanket.

In the foregoing detailed description, the invention has been described with reference to specific embodiments. However, it may be appreciated that various modifications and changes can be made without departing from the scope of the invention as set forth in the appended claims. Although embodiments of the invention are described in the context of a hospital operating room, it is contemplated that some embodiments of the invention may be used in other environments. Those embodiments of the present invention, which are not intended for use in an operating environment and need not meet stringent FDA requirements for repeated used in an operating environment, need not including particular features described herein, for example, related to precise temperature control. Thus, some of the features of preferred embodiments described herein are not necessarily included in preferred embodiments of the invention which are intended for alternative uses.

The invention claimed is:

1. An electric heating blanket, comprising:
    a flexible sheet-like heating element;
    a shell covering the heating element and comprising at least two sheets of flexible material;
    a first weld coupling the two sheets of flexible material together about an outer periphery of the flexible heating element to hermetically seal the heating element therebetween; and
    a second weld coupling the two sheets of flexible material together about a periphery of the sheets to seal the peripheries of the two sheets together, wherein an air pocket is created between the two sheets of flexible material and between the first and second welds.

2. The electric heating blanket of claim 1, wherein the two sheets comprise PVC.

3. The electric heating blanket of claim 1, wherein each sheet comprises a strengthening layer and a second layer.

4. The electric heating blanket of claim 3, wherein the strengthening layer comprises woven nylon and the second layer comprises a water-resistant material that facilitates the welds.

5. The electric heating blanket of claim 4, wherein each sheet further comprises a third layer on an outside surface of the sheet, the third layer including a water-resistant material.

6. The electric heating blanket of claim 5, wherein the third layer comprises an anti-slip surface.

7. The electric heating blanket of claim 1, wherein the two sheets further comprise at least one strap.

8. The electric heating blanket of claim 7, wherein the at least one strap comprises a reinforcing layer.

9. The electric heating blanket of claim 8, wherein the at least one strap is integrally formed with at least one of the sheets.

10. The electric heating blanket of claim 8, further including an attachment post on which the strap may be secured.

11. The electric heating blanket of claim 10, wherein the attachment post is integrally formed with an anchoring layer that is thermally bonded between the sheets.

12. The electric heating blanket of claim 1, wherein the heating element is held in position between the two sheets without using connectors that pierce the two sheets.

13. The electric heating blanket of claim 12, wherein the two sheets include a hole passing through the welds to form a hanging point for the electric heating blanket.

14. The electric heating blanket of claim 12, wherein ribbing or piping, forming a soft peripheral edge to the electric heating blanket, extends beyond the edges of the two sheets and is held in place via the welds.

15. The electric heating blanket of claim 1, wherein magnets are retained in place between the two sheets of flexible material and between the first and second welds, the magnets being usable to hold the edges of the blanket together, whereby the blanket may be wrapped about a patient and the edges may be held together via the magnets.

16. The electric heating blanket of claim 1, further comprising:
    a first conductive bus bar coupled to the heating element and extending alongside a first edge of the heating element, the first bus bar being adapted for coupling to a power source for powering the heating element; and
    a second conductive bus bar coupled to the heating element and extending alongside a second edge of the heating element, the second bus bar being adapted for coupling to the power source for powering the heating element.

17. The electric heating blanket of claim 16, wherein
    the heating element is stitched to the first bus bar with a first row of electrically conductive stitching; and
    the heating element is stitched to the second bus bar with a second row of electrically conductive stitching.

18. The electric heating blanket of claim 17, further comprising:
    a first electrically insulating member interposed between the first conductive bus bar and the flexible heater and being secured therebetween by the first row of conductive stitching, the first electrically insulating member preventing direct electrical contact between the first conductive bus bar and the flexible heater; and
    a second electrically insulating member interposed between the second conductive bus bar and the flexible heater and being secured therebetween by the second row of electrically conductive stitching, the second electrically insulating member preventing direct electrical contact between the first conductive bus bar and the flexible heater.

19. The electric heating blanket of claim 1, wherein the heating element has a surface area of generally uniform electrical resistance per unit area such that the heating element produces a substantially uniform watt density output across the surface area when the element is electrically powered.

20. The electric heating blanket of claim 19, further comprising:
    a temperature sensor coupled to the heating element at a first location thereof where the heating element will be in conductive contact with a body when the blanket is draped over the body, the first location defining a first temperature zone of the surface area of the element;
    a temperature controller coupled to the temperature sensor; and
    an electric power source coupled to the heating element and to the temperature controller, the power source being controlled by the controller, according to a sensed temperature of the first temperature zone, as sensed by the temperature sensor, in order to maintain a first temperature of the first temperature zone lower than a second temperature of a second temperature zone of the surface area of the heating element, the second temperature zone being defined by a second location of the heating element that is not in conductive contact with the body when the blanket is draped over the body.

21. The electric heating blanket of claim 1, further comprising:
an array of temperature sensors positioned over the surface of the heating element to collect temperature readings of the heating element.

22. The electric heating blanket of claim 1, wherein the heating element comprises a nonconductive layer coated with a conductive material.

23. The electric heating blanket of claim 22, wherein the nonconductive layer of the flexible heater comprises a woven polymer and the conductive material comprises one of: polypyrrole, carbonized ink and metalized ink.

24. The electric heating blanket of claim 22, wherein the nonconductive layer of the flexible heater comprises a non-woven polymer and the conductive material comprises one of: polypyrrole, carbonized ink and metalized ink.

25. The electric heating blanket of claim 1, further comprising:
a flexible insulating layer extending over a first side of the heating element and covered by the shell.

26. The electric heating blanket of claim 25, wherein the first side is a top side.

27. The electric heating blanket of claim 25, wherein the insulating layer provides at least one of thermal insulation and electrical insulation.

28. The electric heating blanket of claim 25, wherein the insulating layer comprises one of a foam, a high loft non-woven fibrous material, a low loft non-woven fibrous material, a woven fabric, such as cotton or fiberglass, a thin plastic film, cotton, a non-flammable material, cotton and fiberglass.

29. The electric heating blanket of claim 25, further comprising:
a first conductive bus bar coupled to the heating element and extending alongside a first edge of the heating element, the first bus bar being adapted for coupling to a power source for powering the heating element;
a second conductive bus bar coupled to the heating element and extending alongside a second edge of the heating element, the second bus bar being adapted for coupling to the power source for powering the heating element; and
the insulating layer extending over the first and second bus bars.

30. The electric heating blanket of claim 29, wherein the heating blanket is a pad.

31. The electric heating blanket of claim 30, wherein the heating blanket is flexible.

32. The electric heating blanket of claim 1, further comprising:
at least one securing strip coupled to the heating element, the at least one securing strip being coupled to the shell by the thermal bond.

33. The electric heating blanket of claim 1, wherein the heating blanket is a pad.

34. The electric heating blanket of claim 1, wherein the two sheets comprise urethane to facilitate the welds.

35. The electric heating blanket of claim 1, wherein the two sheets comprise a weldable polymeric layer to facilitate the welds.

36. The electric heating blanket of claim 1, wherein the second weld couples the two sheets of flexible material together about the entire periphery of the sheets.

37. The electric heating blanket of claim 1, wherein the second weld couples the two sheets of flexible material together about a perimeter edge of the two sheets.

38. The electric heating blanket of claim 1, wherein the second weld couples the two sheets of flexible material together about at least a portion of the entire periphery of the two sheets.

39. The electric heating blanket of claim 1, wherein the first weld and the second weld are welded together at portions of the periphery of the sheets.

40. The electric heating blanket of claim 1, wherein the first weld and the second weld merge together at portions of the periphery of the sheets.

* * * * *